United States Patent
Tockert et al.

(10) Patent No.: US 9,982,946 B2
(45) Date of Patent: May 29, 2018

(54) OPTICAL MONITORING SYSTEM FOR OBSERVING INTERNAL CONDITIONS IN THE TUYERE ZONE OF A BLAST FURNACE

(71) Applicant: Paul Wurth S.A., Luxembourg (LU)

(72) Inventors: Paul Tockert, Berbourg (LU); Benoît Jung, Thionville (FR)

(73) Assignee: PAUL WURTH S.A., Luxembourg (LU)

( * ) Notice: Subject to any disclaimer, the term of this patent is extended or adjusted under 35 U.S.C. 154(b) by 0 days. days.

(21) Appl. No.: 15/549,822

(22) PCT Filed: Feb. 9, 2016

(86) PCT No.: PCT/EP2016/052663
§ 371 (c)(1),
(2) Date: Aug. 9, 2017

(87) PCT Pub. No.: WO2016/128366
PCT Pub. Date: Aug. 18, 2016

(65) Prior Publication Data
US 2018/0031323 A1    Feb. 1, 2018

(30) Foreign Application Priority Data
Feb. 10, 2015  (LU) .......................... 92653

(51) Int. Cl.
*G01N 21/00*    (2006.01)
*F27D 21/02*    (2006.01)
(Continued)

(52) U.S. Cl.
CPC ............. *F27D 21/02* (2013.01); *C21B 7/163* (2013.01); *C21B 7/24* (2013.01); *C21C 5/4673* (2013.01); *G01N 21/954* (2013.01)

(58) Field of Classification Search
CPC .. F27D 21/02; C21B 7/16; C21B 7/24; C21C 5/46; G01N 21/954; G01N 21/64;
(Continued)

(56) References Cited

U.S. PATENT DOCUMENTS 5,397,108 A * 3/1995 Alexander ................ C21B 7/24
266/100

FOREIGN PATENT DOCUMENTS

| CN | 2858661 Y | 1/2007 |
|---|---|---|
| CN | 202688355 U | 1/2013 |
| LU | 90610 A1 | 1/2002 |

OTHER PUBLICATIONS

International Search Report dated May 2, 2016 re: Application No. PCT/EP2016/052663; pp. 1-3.
(Continued)

*Primary Examiner* — Abdullahi Nur
(74) *Attorney, Agent, or Firm* — Cantor Colburn LLP

(57) ABSTRACT

The invention relates to an optical monitoring system (26) for monitoring operating conditions in a tuyere zone of a blast furnace. This system comprises a light deflecting device (40) with a peep sight (28) arranged in a first face (46) of the light deflecting device (40) and an optical sensor (30) arranged in a second face (48) of the light deflecting device (40). A light deflector (41) is arranged within the light deflecting device (40) for directing incident light from the tuyere zone towards the peep sight (28) and towards the optical sensor (30). The light deflecting device (40) comprises a housing (56) with a spherical body (60) rotatably arranged therein. The spherical body (60) comprises three passages: a first passage (62) which is, when the light deflecting device (40) is connected to the rear portion of the blowpipe (18), facing the tuyere for allowing incident light from the tuyere zone to enter the spherical body (60); a second passage (70) facing the peep sight (28); a third passage (72) facing the optical sensor (30). The first, second and third passages (62, 68, 72) are configured so as to meet each other within the spherical body (60). The light deflector (41) is arranged within the spherical body (60) at the intersection of the first, second and third passages (62, 68, 72). Furthermore, the light deflecting device (40) comprises an opening (76) in a third face (50) of the housing (56) for accessing the spherical body (60) for allowing rotation of the
(Continued)

spherical body (60) within the housing (56). The spherical body (60) comprises a socket (78) facing the opening (76) in the third face (50). The opening (76) is a guiding slot (86) whose width is substantially the same as a diameter of the socket (78).

15 Claims, 3 Drawing Sheets

(51) Int. Cl.
     *C21B 7/16*       (2006.01)
     *G01N 21/954*       (2006.01)
     *C21C 5/46*       (2006.01)
     *C21B 7/24*       (2006.01)

(58) Field of Classification Search
     CPC ...... G01N 21/68; G01J 3/02; H01J 37/32935;
                 G02B 23/24; A61B 5/1076; G01M 3/38
     See application file for complete search history.

(56) References Cited

OTHER PUBLICATIONS

Written Opinion dated May 2, 2016 re: Application No. PCT/EP2016/052663; pp. 1-6.

\* cited by examiner

OPTICAL MONITORING SYSTEM FOR OBSERVING INTERNAL CONDITIONS IN THE TUYERE ZONE OF A BLAST FURNACE

TECHNICAL FIELD

The present disclosure generally relates to an optical monitoring system for observing internal conditions in the tuyere zone of a blast furnace.

BACKGROUND

As is well known, blast furnaces generally comprise multiple fluid injection paths, whereby hot gas is injected into the blast furnace via blowpipes and tuyeres. If material has accumulated in front of the tuyere nozzle, an injection port may be blocked. If left undetected, the fluid may no longer exit the blowpipe, thus not being fed into the blast furnace. Furthermore, tuyeres are often used to feed pulverized coal into the blast furnace. Should an injection port be blocked this would of course prevent pulverized coal to enter the blast furnace and may cause an accumulation of the pulverized coal in the tuyere and the blowpipe.

In order to observe whether or not a tuyere is blocked, a tuyere sight hole, often also referred to as a peephole or peep sight, is arranged at the rear end of the blowpipe. Such a peep sight allows an operator to look right through the blowpipe and the tuyere zone, thus inspecting the condition of the tuyere and detecting if a blockage has occurred in the tuyere zone.

The tuyere also provides a window into the interior of the blast furnace. Thus, the peep sight also allows observing internal conditions of the blast furnace. The peep sight therefore allows monitoring the condition and the temperature evolution in the heart of the blast furnace. The operator can thus detect disfunctionings in the operation of the blast furnace and act accordingly.

In order to facilitate monitoring and provide for a more automated system, electronic monitoring devices, such as tuyere video cameras have been developed which continuously monitor the light emitted through the peep sight and provide feedback to the operator.

In order to allow both monitoring systems to work simultaneously, i.e. allow visual monitoring with the naked eye and electronic monitoring, a light deflector can be installed to deflect part of the incident light towards the electronic monitoring device while allowing part of the light to pass to the peep sight for visual monitoring. In order for such a light deflector to adequately direct light to both the electronic monitoring device and the peep sight, the orientation of the light deflector is of importance. An adjustment mechanism for the light deflector is thus beneficial, in particular because there may be relative movement between the various components due to important temperature differences of the blast furnace installation. Indeed, generally the electronic monitoring device, the peep sight and the light deflector would be installed while the blast furnace is at a standstill. As the blast furnace is brought up to its working temperature, this temperature difference causes relative movement between various elements and may cause misalignment of the light deflector. Adjustment of the light deflector then becomes necessary. Also, the adjustment of the light deflector may be useful to compensate for any constructional geometrical errors that may occur during production of the monitoring system.

In LU 90 610, an optical sensor is arranged perpendicular to the light path from the tuyere to the peep sight. A light deflector formed by a glass plate is arranged in a cylindrical housing to deflect part of the light to the optical sensor. The glass plate forms an angle of about 45° with respect to the light path between the tuyere to the peep sight. For adjusting means, the glass plate can be independently rotated in two directions inside the cylindrical housing. An eccentric screw can set the position of a first support plate, mounted rotatably around an axis perpendicular to the central axis on a rear face of the cylindrical housing. A second adjustment screw allows together with a spring a second support plate, mounted on the first support plate, to swivel the glass plate about a swiveling axis. As LU 90 610 requires access to two separate adjustment screws arranged within the housing, its adjustment mechanism may be considered cumbersome by some.

BRIEF SUMMARY

The disclosure provides a compact and easy adjustable optical monitoring system, which is capable of observing the internal conditions in the tuyere zone of a blast furnace that does not present the above-described drawbacks.

An optical monitoring system is provided for monitoring operating conditions in a tuyere zone of a blast furnace. This system comprises a light deflecting device configured for connection to a rear portion of a blowpipe such that the tuyere, the blowpipe and the light deflecting device are positioned along a common axis. A peep sight is arranged in a first face of the light deflecting device for allowing an operator to monitor the operating conditions in the tuyere zone with the naked eye. Furthermore, an optical sensor is arranged in a second face of the light deflecting device for electronic monitoring of the operating conditions in the tuyere zone. A light deflector is arranged within the light deflecting device for directing incident light from the tuyere zone towards the peep sight and towards the optical sensor.

The light deflecting device comprises a housing with a spherical body rotatably arranged therein. The spherical body comprises three passages: a first passage which is, when the light deflecting device is connected to the rear portion of the blowpipe, facing the tuyere for allowing incident light from the tuyere zone to enter the spherical body; a second passage facing the peep sight; a third passage facing the optical sensor. The first, second and third passages are configured so as to meet each other within the spherical body. The light deflector is arranged within the spherical body at the intersection of the first, second and third passages. Furthermore, the light deflecting device comprises an opening in a third face of the housing for accessing the spherical body for allowing rotation of the spherical body within the housing.

By installing the light deflector in a spherical body arranged in a housing, the adjustment of the light deflector within the housing can be achieved easily and quickly from the outside of the housing, thus without the need to access the interior of the housing as would e.g. be required to access the screws of the system according to LU 90 610.

The optical monitoring system of the present disclosure is easily manufactured by usual tooling. The passages for allowing light to pass through the spherical body can easily be bored through the body.

The present disclosure also reduces the number of components necessary for the optical monitoring system. This of course has a positive impact on manufacturing costs. Problems caused by interaction between various components are also reduced.

The optical monitoring system thus provides a particularly easy and robust construction, which is furthermore accompanied by reduced manufacturing and maintenance costs.

The spherical body comprises a socket facing the opening in the third face of the housing allowing the insertion of an adjustment tool for rotating the spherical body within the housing. The socket and the adjustment tool are preferably self-locking and/or have any connection shape capable of transmitting a torque. The socket advantageously has a non-circular cross-section and the adjustment tool is preferably a key having a corresponding cross-section. The cross-section of the socket may be of any shape capable of rotating the socket about its axis, such as e.g. triangular, square, cross-shaped, and many more. Most advantageously, the socket has hexagonal cross-section and the adjustment tool is a hexagonal key, generally also referred to as Allen key. The use of an adjustment tool engaging a socket allows for an easy translational movement of the outer surface of the spherical body. The hexagonal socket and hexagonal key configuration furthermore allows for the rotation of the spherical ball about an axis comprising the socket.

According to an aspect of the present disclosure, the opening in the third face of the housing is a guiding slot, whose width is substantially the same as a diameter of the socket wherein a linear movement of the socket along the guiding slot causes the spherical body to rotate about a first rotation axis; and wherein a rotational movement of the socket causes the spherical body to rotate about a second rotation axis. The first rotation axis is preferably substantially perpendicular to the second rotation axis. While the adjustment tool is inserted in the socket, translational movement of the outer surface of the spherical body in a direction other than that allowed by the guiding slot is prevented. In other words, translation of the outer surface of the spherical body is allowed only in one direction, whereby the position of the first rotation axis is predefined by the configuration of the guiding slot. The hexagonal socket and hexagonal key configuration allows rotating the spherical ball about the second rotation axis, which comprises the socket and the center of the spherical body. Consequently, the light deflector can be adjusted in all directions, by simply inserting a hexagonal key and rotating the latter and sliding it within the guide slot.

Advantageously, the light deflector is fixedly arranged within the spherical body, e.g. through applying high temperature glue between the light deflector and the spherical body. Other appropriate fixing means may be readily available and may be used as alternative.

The light deflecting device preferably further comprises a spring element arranged between the spherical body and the housing for maintaining the spherical body in place through friction. The spring element may be an annular spring, preferably a helical spring washer. The spring element pushes the spherical body against the inside surface of the housing thus causing friction which prevents the spherical ball from moving or rotating within the housing. The force of the spring element is chosen such that any movement of the spherical body is prevented unless outside force is applied via the adjustment tool.

Preferably, the housing comprises a removable mounting face for insertion and/or removal of the spherical body. The removable mounting face may be the first face of the housing comprising the peep sight.

A ring shaped seat element is preferably arranged between the spherical body and the mounting face. Such a ring shaped seat element is configured such that its side facing the spherical body acts as a seat for the spherical body. The spring element is preferably arranged between the mounting face and the ring shaped seat element such that the ring shaped seat element is pushed against the spherical body.

The spherical body may comprise a slot for receiving the light deflecting device therein.

The peep sight is advantageously formed by a glass plate sandwiched between the first face of the housing and the ring shaped seat element. A first annular seal may be arranged between the ring shaped seat element and the glass plate, while a second annular seal may arranged between the glass plate and the first face.

BRIEF DESCRIPTION OF THE DRAWINGS

Preferred embodiments of the disclosure will now be described, by way of example, with reference to the accompanying drawings, in which.

DETAILED DESCRIPTION

Figure 1:
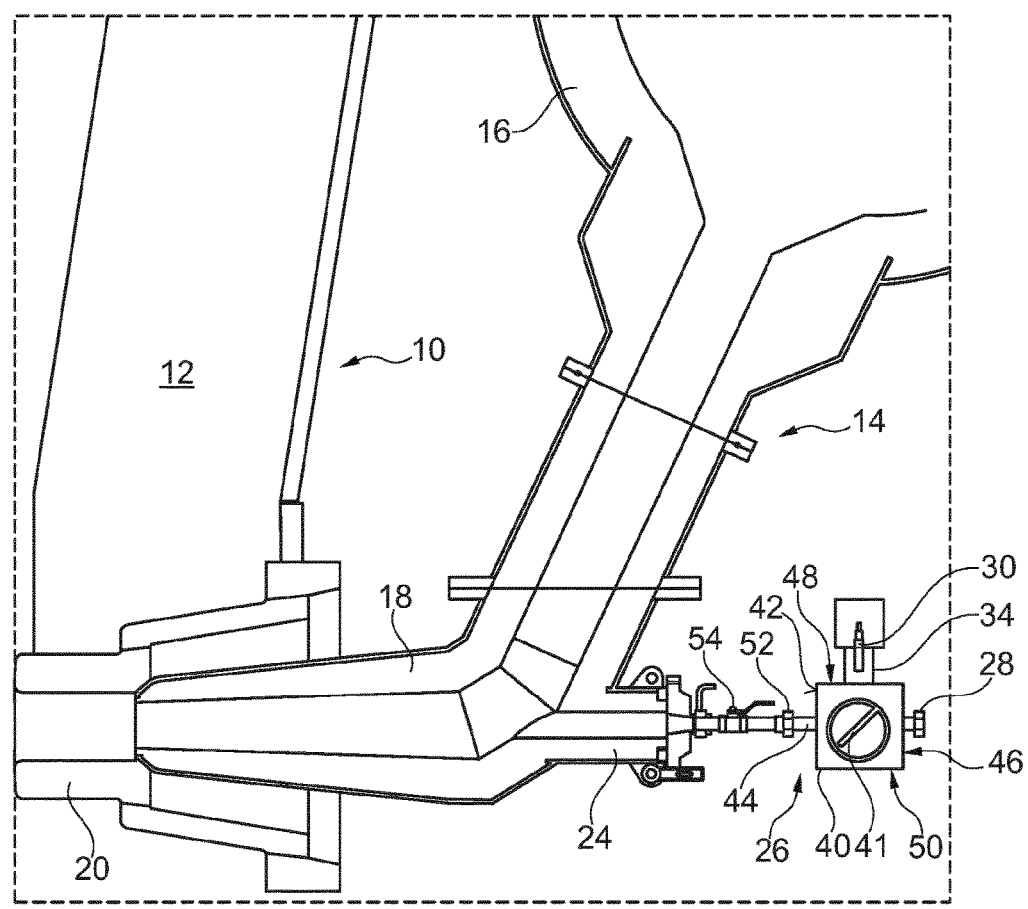
FIG. 1 is a side cross-sectional view of a blast furnace tuyere with a blowpipe to which an optical monitoring system according to the present disclosure is connected.

FIG. 1 is a side cross-sectional view of a blast furnace tuyere arrangement with an optical monitoring system according to the present disclosure connected thereto. FIG. 1 shows a blast furnace 10 with a blast furnace wall 12, and a hot blast system 14 composed of a tuyere 20 in the tuyere zone, a blowpipe 18 and a bustle pipe 16. The bustle pipe 16 encircles the blast furnace and distributes a fluid, generally hot air, into the blast furnace 10 through tuyeres 20 that are equally spaced around the circumference of the furnace 10.

The blowpipe 18 comprises, in its elbow portion, an extension pipe 24. An optical monitoring system 26 is connected to the extension pipe 24 and has the same axis as the blowpipe 18. The optical monitoring system 26 comprises a peep sight 28, allowing an operator to look through the blowpipe 18 into the tuyere 20. The peep sight 28 is generally in axial alignment with the central axis of the blowpipe 18. An optical sensor 30 furthermore allows for electronic monitoring of the blowpipe 18. The optical sensor 30 is mounted in a lateral housing 34.

Also illustrated schematically in FIG. 1 is a light deflecting device 40 arranged in the axial light path coming from the tuyere 20. The light deflecting device 40, which has a light deflector 41 arranged therein, comprises a connection face 42 with a connection pipe 44 for connection to the extension pipe 24 of the blowpipe 18. The light deflecting device 40 further comprises a first face 46, generally arranged opposite the connection face 42, comprising the peep sight 28; and a second face 48 comprising the optical sensor 30. The light deflecting device 40 also comprises a third face 50 for adjusting the light deflector 41 as further described below.

The light deflector 41 is arranged at the intersection of the axis of the optical sensor 30 and the central axis of the blow pipe 18 and deflects a portion of the light towards the optical sensor 30, while also allowing a portion of the light to reach the peep sight 28. The incident light from the furnace is thus partly directed to the optical sensor 30, where it receives sufficient light to monitor the tuyere 20. The deflected light can be bundled, via a lens for example, so as to concentrate the deflected light and allow light intensity measurements.

It should be understood that instead of an optical sensor 30, a video camera, a photosensitive detector, an image scanning camera or the like can be installed into the optical sensor 30.

It is noted also that the light deflecting device 40 shown in FIG. 1 is represented schematically and should not be interpreted as being to scale.

A glass window 52 may be arranged between the extension pipe 24 and the connection pipe 44 of the light deflecting device 40, so as to protect the latter from the internal harsh environment of the blast furnace. An optical filter (not shown) may also be placed together or incorporated within the peep sight 28, in order to protect the operator's eye from the brightness of the light emitted from the furnace.

FIG. 1 also shows a shut-off valve 54 arranged between the optical monitoring system 26 and the extension pipe 24 of the blowpipe 18. The shut-off valve 54 allows isolating the optical monitoring system 26 from the blowpipe 18, e.g. when maintenance work is carried out.

Figure 2:
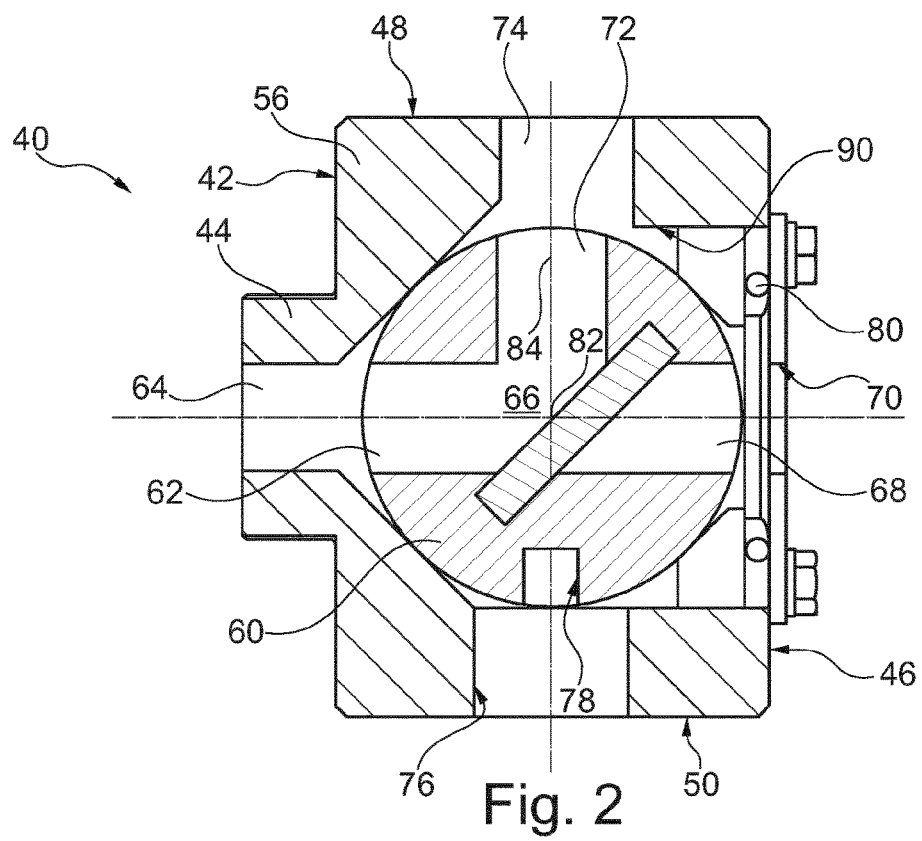
FIG. 2 is a side cross-sectional view through the light deflecting device of the optical monitoring system of FIG. 1.

The present disclosure can be more closely described by referring to FIG. 2, which shows the light deflecting device 40 in more detail. The light deflecting device 40 is formed by a housing 56 comprising six faces, including the aforementioned connection face 42 and first, second and third faces 46, 48, 50.

A spherical body 60 is rotatably arranged within the housing 56 and comprises passages for allowing light to pass through the spherical body 60. A first passage 62, which is in alignment with a first aperture 64 in the connection face 42 of the housing 56, is used to allow light to be fed to a central region 66 of the spherical body 60. A second passage 68, which is in alignment with a second aperture 70 in the first face 46 of the housing 56, is used to allow light to be fed from the central region 66 to the peep sight 28. A third passage 72, which is in alignment with a third aperture 74 in the second face 48 of the housing 56, is used to allow light to be fed from the central region 66 to the optical sensor 30.

In the central region 66 of the spherical body 60, the light deflector 41 is arranged such that incident light from the tuyere zone is directed towards the peep sight 28 as well as towards the optical sensor 30. Indeed, the light deflector 41, which may be a translucent glass, a coated glass, a colored glass plate, a semi-transparent mirror, a glass prism or a polarization element, allows a portion of the incident light to pass through the light deflector 41 towards the peep sight 28, while reflecting a portion of the incident towards the optical sensor 30.

Figure 5:
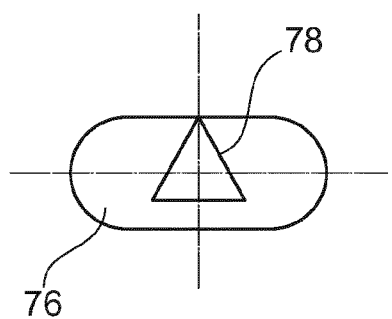
FIG. 5 is an enlarged view of FIG. 4 according to another embodiment of the socket of the spherical body.
Figure 6:
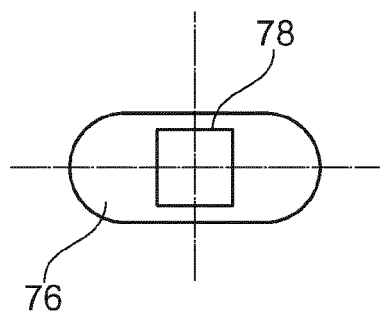
FIG. 6 is an enlarged view of FIG. 4 according to another embodiment of the socket of the spherical body.

In the third face 50 of the housing 56, an opening 76 is arranged for accessing the spherical body 60 from the outside, so as to adjust the position of the spherical body 60 if needed. For adjustment purposes, the spherical body 60 comprises, in a region facing the opening 76, a hexagonal socket 78, which can be engaged by an adjustment tool, such as a hexagonal key (not shown). The opening 76, which is preferably in the form of a guiding slot, and the hexagonal socket 78 are also shown of FIG. 4. Alternative socket shapes are shown in FIGS. 5 and 6. FIG. 5 shows a socket with triangular cross-section, while FIG. 6 shows a socket with square cross-section. Many alternative shapes may be envisaged.

Figure 4:
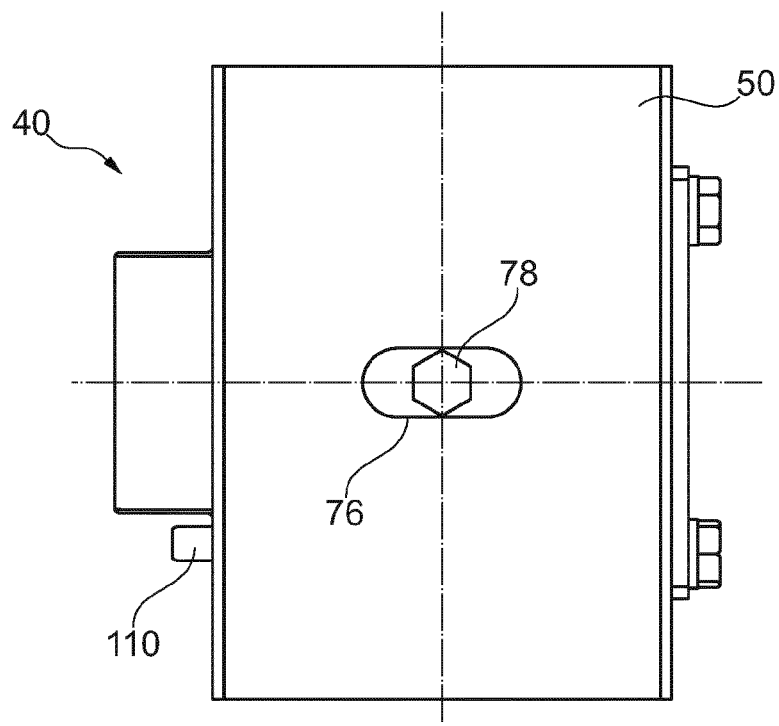
FIG. 4 is a view of the bottom of the light deflecting device of FIG. 2.

While the opening 76 is shown in FIG. 4 as a substantially rectangular guiding slot, it should be noted that different shapes and sizes should not be excluded; these may provide different adjusting possibilities. The inventors have however chosen a guiding slot as preferred solution as it allows a particularly advantageous adjustment of the spherical body 60. To this effect, the guiding slot has a width substantially corresponding to the diameter of the hexagonal socket 78. With the adjustment tool inserted in the hexagonal socket 78, translational movement of the hexagonal socket 78 is limited to the direction defined by the guiding slot 76. Indeed, such translational movement allows a rotation of the spherical body 60 about a first rotational axis 82 as indicated in FIG. 2. On the other hand, a rotational movement of the adjustment tool, and consequently of the hexagonal socket 78, allows a rotation of the spherical body 60 about a second rotational axis 84 as shown in FIG. 2. The choice between translational and rotational movement allows the user to have good control over the adjustment process as rotation about the first and second rotational axis 82, 84 can be performed independently from one another.

The first face 46 of the housing 56 can be configured as a removable mounting face for allowing the spherical body 60 to be inserted into and removed from the housing 56. The configuration of the mounting face and the mounting process can be more closely described by referring to FIG. 3, which shows a cross-sectional view from above through the housing 56.

Firstly, the spherical body 60 is provided with a lateral slot 86 which allows the light deflector 41 to be inserted into the spherical body 60 while the latter is not within the housing. Once inserted, the light deflector 41 is immobilized within the spherical body 60 by appropriate fixing means such as e.g. high temperature glue. Other appropriate fixing means may be readily available and may be used as alternative.

Once the spherical body 60 and light deflector 41 are assembled, the spherical body 60 can be inserted into a cavity 88 in the housing 56 through a hole 90 in the first face 46; the hole 90 and the cavity 88 having a cross-section essentially corresponding to the diameter of the spherical body 60.

After insertion of the spherical body 60, the latter is adjusted such that the first, second and third passages 62, 68, 72 are in alignment with the respective first, second and third apertures 64, 70, 74. In order to close the hole 90 and maintain the spherical body 60 within the housing 56, a ring shaped seat element 92 is placed into the hole 90. The seat element 92 is configured such that its side facing the spherical body 60 acts as a seat for the spherical body 60. The ring shaped seat element 92 is held in place by an end plate 94 connected to the housing 56 by adequate fixing means, such as e.g. screws 96.

Before connecting the end plate 94, the spring element 80 is arranged between the ring shaped seat element 92 and the end plate 94. Such a spring element 80, which is preferably an annular spring, most preferably a helical spring washer, pushes the ring shaped seat element 92 against the spherical body 60, thereby immobilizing the latter. The spring element 80 is however sufficiently resilient to allow rotation of the spherical body 60 when outside force is applied via the adjustment tool.

Figure 3:
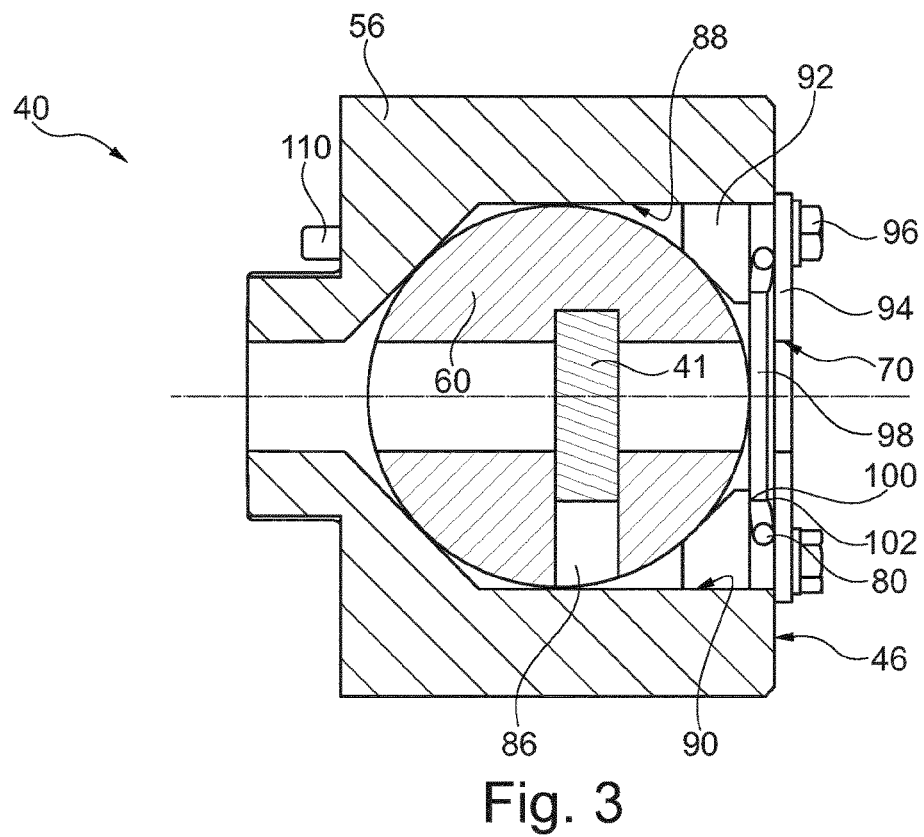
FIG. 3 is a cross-sectional view from above through the light deflecting device of FIG. 2.

The peep sight 28 can be piece of piping with a glass plate at the end as shown e.g. in FIG. 1. Preferably, however, the peep sight 28 is integrated within the mounting face as shown in FIG. 3. To this effect, a glass plate 98 is sandwiched between the ring shaped seat element 92 and the end plate 94. First and second annular seals 100, 102 are arranged between the glass plate 98 and respectively the ring shaped seat element 92 or end plate 94.

A centering pin 110 (as visible on FIGS. 3 and 4) is arranged on the connection face 42 for engaging a corresponding hole on the extension pipe 24. Such a centering pin 110 allows ensuring the correct positioning of the light deflecting device 40 with respect to the extension pipe 24.

The invention claimed is:

1. Optical monitoring system for monitoring operating conditions in a tuyere zone of a blast furnace, said optical monitoring system comprising:
    a light deflecting device configured for connection to a rear portion of a blowpipe such that the tuyere, the blowpipe and the light deflecting device are positioned along a common axis;
    a peep sight arranged in a first face of said light deflecting device for allowing an operator to monitor the operating conditions in the tuyere zone with an unaided eye;
    an optical sensor arranged in a second face of said light deflecting device for electronic monitoring of the operating conditions in the tuyere zone;
    a light deflector arranged within said light deflecting device for directing incident light from the tuyere zone towards said peep sight and towards said optical sensor
    wherein said light deflecting device comprises a housing with a spherical body rotatably arranged therein,
    wherein said spherical body comprises,
        a first passage which is, when said light deflecting device is connected to the rear portion of the blowpipe, facing the tuyere for allowing incident light from the tuyere zone to enter the spherical body;
        a second passage facing said peep sight;
        a third passage facing said optical sensor;
        wherein said first, second and third passages are configured so as to meet each other within said spherical body;
    wherein said light deflector is arranged within said spherical body at an intersection of said first, second and third passages;
    wherein said light deflecting device further comprises an opening in a third face thereof for accessing the spherical body and allowing rotation of the spherical body within said housing;
    wherein said spherical body comprises a socket facing said opening in said third face of said light deflecting device allowing the insertion of an adjustment tool for rotating the spherical body within said housing;
    wherein said opening in said third face of said light deflecting device is a guiding slot whose width is substantially the same as a diameter of said socket;
    wherein a linear movement of said socket along the guiding slot causes said spherical body to rotate about a first rotation axis, and
    wherein a rotational movement of said socket causes said spherical body to rotate about a second rotation axis.

2. The optical monitoring system according to claim 1, wherein said socket and said adjustment tool are self-locking and/or have any connection shape capable of transmitting a torque.

3. The optical monitoring system according to claim 1, wherein said socket has non-circular cross-section and said adjustment tool is a key with corresponding cross-section.

4. The optical monitoring system according to claim 2, wherein said socket has hexagonal cross-section and said adjustment tool is a hexagonal key.

5. The optical monitoring system according to claim 1, wherein said first rotation axis is substantially perpendicular to said second rotation axis.

6. The optical monitoring system according to claim 1, wherein the light deflector is fixedly arranged within said spherical body.

7. The optical monitoring system according to claim 1, further comprising a spring element arranged between said spherical body and said housing for maintaining said spherical body in place through friction.

8. The optical monitoring system according to claim 7, wherein said spring element is an annular spring.

9. The optical monitoring system according to claim 1, wherein said light deflecting device comprises a removable mounting face for insertion and/or removal of said spherical body.

10. The optical monitoring system according to claim 9, wherein said removable mounting face is said first face of said light deflecting device comprising said peep sight.

11. The optical monitoring system according to claim 9, wherein a ring shaped seat element is arranged between said spherical body and said mounting face.

12. The optical monitoring system according to claim 7, wherein said spring element is arranged between a mounting face and said ring shaped seat element.

13. The optical monitoring system according to claim 1, wherein said spherical body comprises a slot for receiving said light deflector therein.

14. The optical monitoring system according to claim 11, wherein said peep sight is formed by a glass plate sandwiched between said first face of said light deflecting device and said ring shaped seat element.

15. The optical monitoring system according to claim 14, wherein
    a first annular seal is arranged between said ring shaped seat element and said glass plate, and
    a second annular seal is arranged between said glass plate and said first face.

* * * * *